United States Patent [19]

Wessels et al.

[11] Patent Number: 5,185,317

[45] Date of Patent: Feb. 9, 1993

[54] METHOD OF FORMING SUPERCONDUCTING TL-BA-CA-CU-O FILMS

[75] Inventors: Bruce W. Wessels, Wilmette; Tobin J. Marks; Darrin S. Richeson, both of Evanston, all of Ill.; Lauren M. Tonge, Sanford, Mich.; Jiming Zhang, Chicago, Ill.

[73] Assignee: Northwestern University, Evanston, Ill.

[21] Appl. No.: 691,477

[22] Filed: Apr. 25, 1991

Related U.S. Application Data

[63] Continuation of Ser. No. 436,078, Nov. 13, 1989, abandoned, which is a continuation-in-part of Ser. No. 158,322, Feb. 19, 1988.

[51] Int. Cl.$^5$ .......................... B05D 5/12; C23C 16/00
[52] U.S. Cl. ........................................ 505/1; 505/734; 505/742; 427/62; 427/255.3; 427/126.3
[58] Field of Search ................... 505/1, 734, 742, 783; 427/62, 63, 255.3, 126.3, 314, 255.2, 255.1, 248.1

[56] References Cited

U.S. PATENT DOCUMENTS

| | | | |
|---|---|---|---|
| 4,097,384 | 6/1978 | Coleman et al. | 250/527 |
| 4,507,643 | 3/1985 | Sunano et al. | 338/34 |
| 4,931,425 | 6/1990 | Kimura et al. | 505/1 |

FOREIGN PATENT DOCUMENTS

| | | |
|---|---|---|
| 0055459 | 7/1982 | European Pat. Off. |
| 63-225528 | 3/1987 | Japan. |
| 310515 | 6/1987 | Japan. |

OTHER PUBLICATIONS

"Laser Deposited High $T_c$ Superconducting Thin Films," Venkatesan, Solid State Technology, Dec., 1987, pp. 39–42.
Strem Chemicals, Inc. Catalog No. 13 (1989), XV, XVI; pp. 112–113.
"Thin Films from Organometallic Compounds," L. A. Ryabova, North Holland Publishing Company, 1981, pp. 587–642.
"Thin Film Studies of Oxides by the Organometallic-CVD Technique," Hari Prakash, Prog. Cystal Growth and Charact., 1983, pp. 371–391.
"Preparation of Nickel and Ni-Zn Ferrite Films by Thermal Decomposition of Metal Acetylacetonates," Itoh et al., Journal of Materials Science 21, 1986, pp. 3677–3680.
"Volatile Alkaline Earth Chelates of Fluorinated Alkanoylpivalylmethanes," Belcher, et al., Anal. Chim. Acta, 1972, pp. 109–115.
"Mixed $\beta$-Diketonates of Copper (II) and Their Base Adducts," Dash, et al., J. Indian Chem. Soc., Oct., 1984, pp. 830–832.
"Studies on Copper (II) Mixed $\beta$-Diketonates and Their Adducts with Nitrogen Bases," Mishra, et al., J. Indian Chem. Soc., Sep., 1984, pp. 802–805.
"Synthesis and Reactions of Substituted Zirconocene and Hafnocene Dimethyls and the Corresponding Dihydrides," Couturier, et al., Journal of Organometallic Chemistry, 1978, pp. C60–C63.
"Preparation and Characterization of Some Rare-Earth Complexes of the Phthalocyanine Radical," Sugimoto, et al., Chemistry Letters, 1983, pp. 1167–1170.
"Rare Earth Chelates of 1,1,1,2,2,3,3, -Heptafluro-7,7, -dimethyl -4,6-octanedione," Springer, Jr., et al., Inorganic Chemistry, Jun., 1967, pp. 1105–1111.

(List continued on next page.)

Primary Examiner—Michael Lusignan
Assistant Examiner—Roy V. King
Attorney, Agent, or Firm—Welsh & Katz, Ltd.

[57] ABSTRACT

A method of forming a superconducting Tl-Ba-Ca-Cu-O film is disclosed, which comprises depositing a Ba-Ca-Cu-O film on a substrate by MOCVD, annealing the deposited film and heat-treating the annealed film in a closed circular vessel with $TlBa_2Ca_2Cu_3O_x$ and cooling to form said superconducting film of $TlO_mBa_2Ca_{n-1}Cu_nO_{2n+2}$, wherein m=1,2 and n=1,2,3.

10 Claims, 4 Drawing Sheets

OTHER PUBLICATIONS

"Fractional Sublimation of Various Metal Chelates of Dipivaloylmethane," Berg, et al., Anal. Chim, Acta, 1972, pp. 117–125.

"Fractional Sublimation of the β-Diketone Chelates of the Lanthanide and Related Elements," Berg, et al., Anal. Chim. Acta, 1968, pp. 101–113.

"Luminescence of Europium Hexafluoroacetylacetonate," Halverson, et al., The Journal of Chemical Physics, May, 1964, pp. 2790–2793.

Chemical Abstracts Search Report of Jan. 16, 1988 and Jan. 20, 1988.

"Formation of Tl–Ca–Ba–Cu–O films by diffusion of Tl into rf-sputtered Ca–Ba–Cu–O," Qiu, et al., Appl. Phys, Lett. 53 (12), Sep. 19, 1988, pp. 1122–1124.

"Organometallic Chemical Vapor Deposition of High $-T_c$ Superconducting," Zhang et al., Northwestern University, Evanston, Illinois, 1 page, Mar. 1989.

"Forming Superconducting Tl–Ca–Ba–Cu–O Thin Films by the Diffusion Method," Lin et al., Japanese Journal of Applied Physics, vol., 28, No. 1, Jan. 1989, pp. L85–L87.

"Formation of Bismuth Strontium Calcium Copper Oxide Superconducting Films by Chemical Vapor Deposition," Yamane, et al., Japanese Journal of Applied Physics, vol., 27, No., 8, Aug. 1988, pp. L149–L1497.

METHOD OF FORMING SUPERCONDUCTING TL-BA-CA-CU-O FILMS

BACKGROUND OF THE INVENTION

This is a continuation of Ser. No. 436,078, filed Nov. 13, 1989, now abandoned, which is a continuation-in-part of Ser. No. 158,322, filed Feb. 19, 1988.

This application relates to a method for forming superconducting materials through the use of chemical vapor deposition and more specifically, it involves a preparation of superconducting films through the use of metal organic chemical vapor deposition of volatile metal organic complexes.

The recent discovery of metal oxide ceramic materials with relatively high superconducting transition temperatures gives rise to a large number potential applications in advanced materials based technologies. However, appropriate practical synthesis and processing methodologies for forming the superconductive ceramics are required for the use of superconducting materials in microelectronics and optoelectronics. Particularly desirable superconductors are $[TlO_mBa_2Ca_{n-1}Cu_nO_{2n+2}; m=1,2; n=1,2,3]$ and $[(BiO)_2Sr_2Ca_{n-1}Cu_nO_x n=1,2,3]$. In general, such superconductive ceramics may be formed as high-quality thin films which are deposited from the gas phase. These thin films have in the past been deposited by physical vapor deposition techniques (ion-sputtering, electron beam, plasma, laser) which employ metal and metal oxide sources. All of these vapor deposition techniques require expensive and/or energy-intensive equipment, must be carried out at high temperatures and do not provide consistently good quality films.

Metal organic chemical vapor deposition has been used for depositing thin films from a vaporizable material. When using metal organic chemical vapor deposition (MOCVD) for depositing metal oxide films on substrates, volatile metal organic precursors must be used. Metal organic precursors for the preparation of the known superconductive ceramic materials which are stable in the gas phase are not generally available. However, the chemical vapor deposition technique does potentially offer the advantage, when compared to the physical methods of film preparation, of higher quality, smoother and more crystalline films produced at lower temperatures and amenability to large scale deposition.

In order to use metal organic chemical vapor deposition, the metal precursor compounds must be sufficiently volatile to transport the compound as a gas to the substrate site. In addition, the metal precursor compound must be relatively stable in the gaseous state. Coordination number and coordinative saturation appear to play a major role in determining the volatility of neutrally charged metal organics. In general, in low oxidation states, a metal complex with non-bulky ligands will attempt to expand its coordination number by coordinating additional ligands, or, when these are unavailable, by forming ligand bridging bonds to neighboring ions. Such bridging bonds lead to polymeric structures, high lattice energies, and low volatility. Two approaches can be used to circumvent this problem. In higher oxidation states, the metal will have a smaller ionic radius, hence a smaller desired coordination number, and generally more non-bridging ligands per metal ion. This usually leads to higher volatility. Another way to reduce intermolecular interactions is by employing sterically bulky and/or fluorinated ligands. Also important, but apparently less critical, is keeping the molecular weight as low as possible.

The compounds selected for use in metal organic chemical vapor deposition must be stable to the thermal conditions necessary to volatilize them. In general, many of the properties which impart volatility additionally afford some resistance to thermal degradation, and therefore, the approaches which should foster higher volatility are also reasonable initial approaches to enhance thermal stability.

As a result, the optimum manner for rendering metal complexes volatile should be complexation by bulky and/or multidentate non-polar hydrocarbon ligands, which saturate the coordination sphere and prevent oligomerization. Ligand fluorination further enhances volatility.

Among the currently known classes of high $T_c$ superconductors, Tl-Ba-Ca-Cu-O materials $[TlO_mBa_2Ca_{n-1}Cu_nO_{2n+2}; m=1,2; n=1,2,3]$ and Bi-Sr-Ca-Cu-O materials $[(BiO)_2Sr_2Ca_{n-1}Cu_nO_x n32 1,2,3]$ exhibit a multiplicity of superconducting phases, high environmental stability, ease of synthesis, and $T_c$ values as high as 122K. Such valuable characteristics have stimulated efforts to prepare high quality Tl-Ba-Ca-Cu-O and Bi-Sr-Ca-Cu-O thin films, and to date activity has largely centered on physical vapor deposition techniques such as sputtering, multi-layer thermal evaporation, and electron beam evaporation. If appropriate molecular precursors and deposition chemistry could be developed, metal organic chemical vapor deposition (MOCVD) would offer an attractive alternative approach and the potential advantages of simplified deposition apparatus, high deposition rates, efficiency in coating complex shapes, excellent film uniformity, and adaptability to deposition under highly oxidizing conditions.

SUMMARY OF THE INVENTION

Accordingly, an object of the subject invention is a method of preparing a superconductive film by metal organic chemical vapor deposition.

Another object of the subject invention is the use of volatile metal organic complexes in the preparation of the superconductive material $[TlO_mBa_2Ca_{n-1}Cu_nO_{2n+2}; m=1,2; n-1,2,3]$ or $[(BIO)_2SR_2Ca_{n-1}CU_nO_x n=1,2,3]$.

Still another object of the subject invention is the use of metal organic chemical vapor deposition with volatile metal organics, and volatile thallium or bismuth compounds, to form either $[TlO_mBa_2Ca_{n-1}Cu_nO_{2n+2}; m=1,2; n=1,2,3]$ or $[(BiO)_2Sr_2Ca_{n-1}Cu_nO_x n32, 1,2,3]$.

These and other objects of the subject invention are attained wherein selected metal organics such as thallium complexes, bismuth complexes, metal organic copper complexes, calcium complexes, barium complexes and strontium complexes are vaporized or sublimed and caused to flow past a heated substrate where they are deposited and then transformed to form a high $T_c$ superconducting film of the formula $[[TlO_mBa_2Ca_{n-1}Cu_nO_{2n+2}; m=1,2; n=1,2,3]$ or $[(BiO)_2Sr_2Ca_{n-1}Cu_nO_x n=1,2,3]$. Films of the high $T_c$ Tl-Ba-Ca-Cu-O or Bi-Sr-Ca-Cu-O superconductor can be prepared by either of two metal organic chemical vapor deposition routes.

To prepare a thallium superconductor film, a Ba-Ca-Cu-O film is first deposited on yttria-stabilized zirconia or other suitable substrate using, for example, the volatile precursors Ba(heptafluorodimethyloctanedionate)$_2$, Ca(dipivaloylmethanate)$_2$, and Cu(acetylacetonate)$_2$. Thallium may next be incorporated in the film either by vapor diffusion using bulk Tl-Ba-Ca-Cu-O as the source, or by metal organic chemical vapor deposition using Tl(cyclopentadienide) or other volatile thallium metal organics as the source.

A bismuth superconductor film is prepared by a metal organic chemical vapor deposition procedure prepared through volatile metal organics precursors such as Cu(acetylacetonate)$_2$, Sr(dipivaloylmethanate)$_2$, Ca(dipivaloylmethanate)$_2$, and triphenyl bismuth or other volatile bismuth-organics. These metal organics are deposited under an argon atmosphere with oxygen and water vapor as reactants, and annealed.

DETAILED DESCRIPTION OF THE INVENTION

For film preparation of metals and their compounds, the following types of metal organics are generally used: Alkyl- and aryl- derivatives of metals, alkoxides and acetylacetonates, carbonyls, cyclopentadienyls, arene-derivatives, arene-carbonyls, and, as suggested herein, -diketonates. The main requirements for such substances used for film preparation are the following:

1. The metal organic should be transformable into the vapor phase without decomposition. The concentration of the metal organic vapor must be sufficient;

2. The metal organic decomposition must be gaseous and should not form side reactions which may lead to contamination of the film and to the formation of non-volatile organic compounds; and 3. The metal organic must be available and relatively stable at room temperature.

Ligand systems which may be utilized in the subject invention to form the stable volatile metal organic compounds are -diketonates of the formula (A):

where R and R' are alkyl or fluoroalkyl groups. More particularly, copper complexes of type A (n31 2), which R=R'=CH$_3$ (acac), R=R'=C(CH$_3$)$_3$ (dpm), and CF$_3$ (hfa) are quite volatile. Type A complexes of M=Tl or Bi (n=3) where R=R'=C(CH$_3$)$_3$, or CF$_3$ are also relatively volatile. In addition, Type A, M=Tl or Bi, complexes with R=C(CH$_3$)$_3$, R'=CF$_2$CF$_2$CF$_3$(fod) are far more volatile than those with dpm. Volatile Type A complexes (n=2) are prepared for barium where (in order of increasing volatility) R=R'=C(CH$_3$)$_3$; R=C(CH$_3$)$_3$, R=CF$_2$CF$_2$CF$_3$; and R=R'=CF$_2$CF$_3$(dfh). The following expressions will be used interchangeably hereinafter:

Dipivaloylmethane complex=dpm=2,2,6,6-tetramethyl-3,5-heptanedione=C$_{11}$H$_{19}$O$_2$
Acetylacetone complex=C$_5$H$_7$O$_2$
Hexaflouroacetylacetone complex=hfa=CF$_3$COCHCOCF$_3$=C$_5$HO$_2$F$_6$
C$_7$HO$_2$F$_{10}$=C$_2$F$_5$COCHCOC$_2$F$_5$=dfh
C$_4$H$_9$COCHCOC$_4$H$_9$C$_3$F$_7$=C$_{14}$H$_{19}$O$_2$F$_7$=fod For Bi and Tl sources, the metal organic compounds of the formula BiR$_3$, TlR' and TlR'$_3$ where R and R' are groups such as alkyl, alkoxide, aryl, halide, and mixtures thereof. For thallium, R' may also be an alicyclic group such as cyclopentadienyl. The preferred compounds are triphenyl bismuth and cyclopentadienyl thallium:

which offer high volatility, air stability, and reactivity with respect to deposition chemistry.

Representative compounds useful in the subject invention and their sublimation temperature are given below in Table I.

TABLE I

| Compound | Approximate Sublimation Temperature (°C.)/ Pressure (torr) |
|---|---|
| Cu(dpm) | 100° C./10$^{-5}$ |
| Cu(hfa)$_2$ | 80° C./10$^{-5}$ |
| Ba(dpm)$_2$ | 170° C./10$^{-5}$ |
| Ba(fod)$_3$ | 170° C./10$^{-5}$ |
| Ba(dfh)$_3$ | 140° C./10$^{-2}$ |
| Tl(dpm)$_3$ | 100° C./10$^{-5}$ |
| Tl(fod)$_3$ | 80° C./10$^{-5}$ |
| Tl(C$_5$H$_5$) | 40° C./10$^{-5}$ |
| Bi(dpm)$_3$ | 110° C./10$^{-5}$ |
| Bi(fod)$_3$ | 85° C./10$^{-5}$ |
| Bi(C$_6$H$_5$)$_3$ | 80° C./10$^{-5}$ |
| Ca(dpm)$_2$ | 150° C./10$^{-5}$ |

Figure 1:
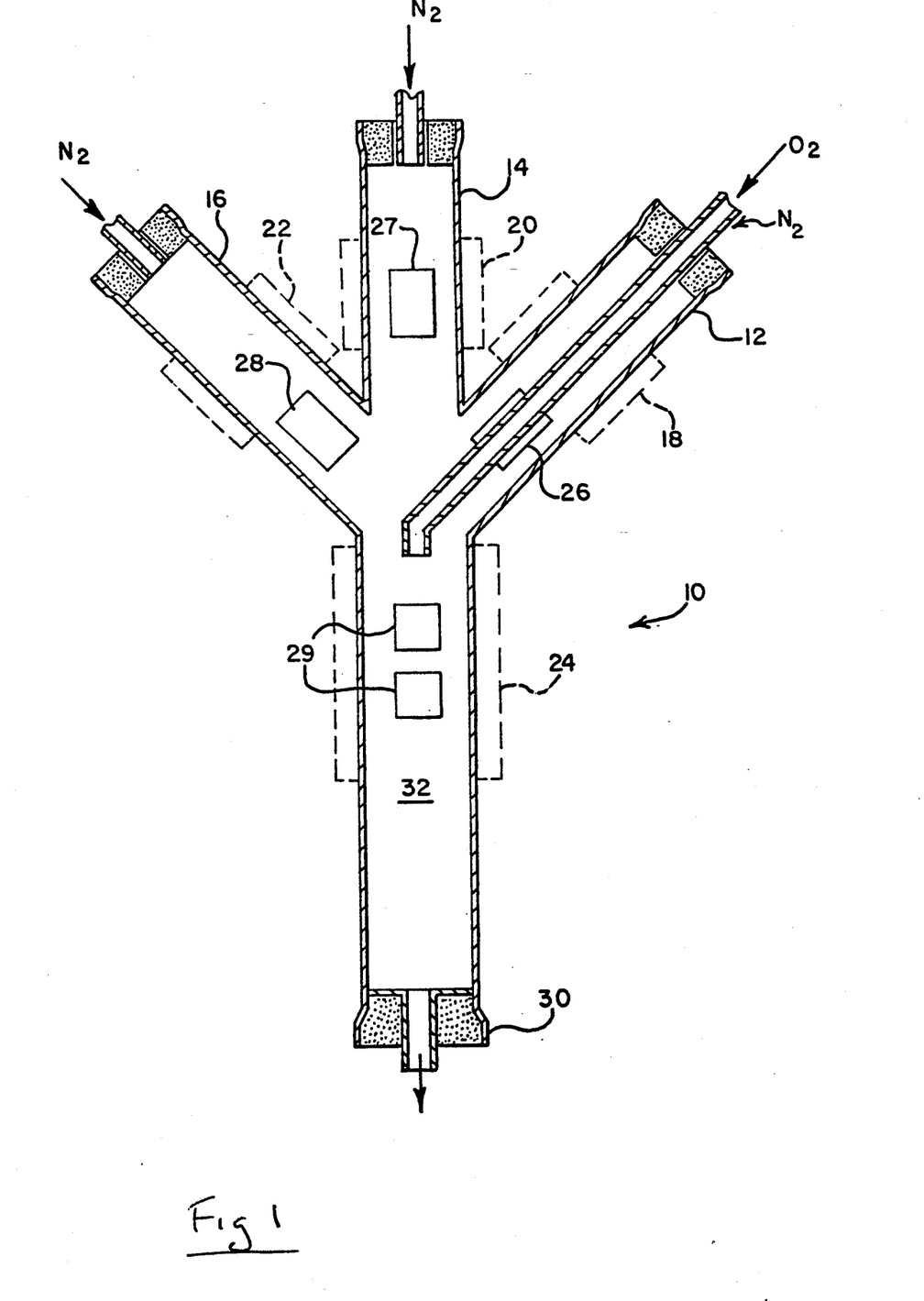
FIG. 1 is a schematic drawing of one type of an organic metal chemical vapor deposition apparatus which might be used in the method of the subject invention.
Figure 2:
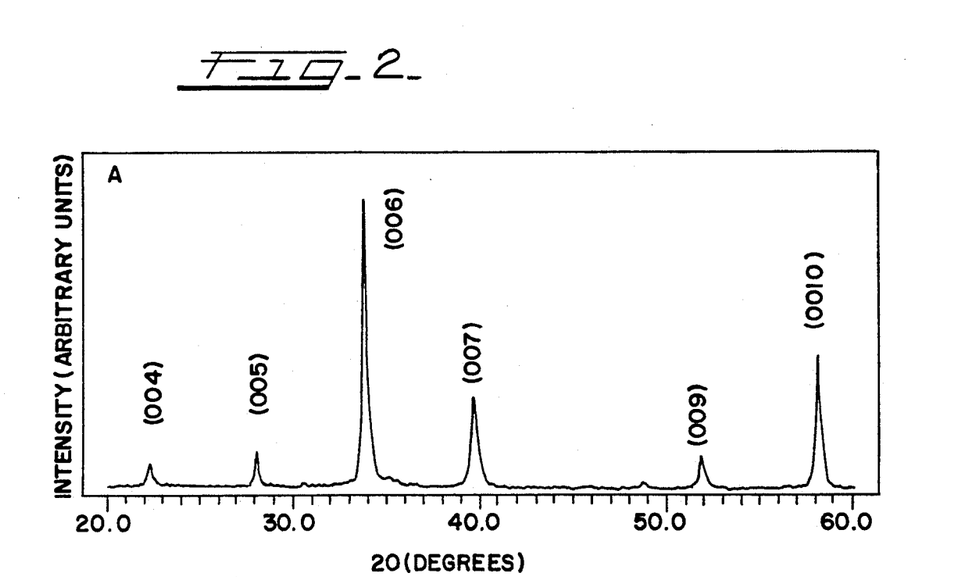
FIG. 2 shows x-ray diffraction patterns of a Tl-Ba-Ca-Cu-O film on yttrium-stabilized zirconia prepared by MOCVD and vapor diffusion of thallium.

The apparatus for film deposition, to a great extent, determines the film growth rate and the productivity of the deposition process. The exact construction of the apparatus generally depends on the method of substrate heating, the geometry and the composition of the substrate, and the properties of the initial substances and requirements of the films to be prepared. As shown in FIG. 1, the chemical vapor deposition apparatus suitable for use in the method of the subject invention is shown at 10 and comprises evaporation chambers 12, 14 and 16 having external heating means, such as heating tape or other resistive heating means 18, 20 and 22 about the respective evaporation chambers 12, 14 and 16, all of which lead to the deposition or reaction chamber 32, which itself is surrounded by a resistive heating means, such as heat tape 24. The number of evaporation chambers may be more or less, as needed. The reaction chamber 32 is preferably constructed of quartz. Within the reaction $Al_2O_3$, $Si_3N_4$, $SiO_2$, MgO, platinum, gold, silver, or stainless steel. Passing through one of the evaporation chambers is a conduit for the introduction of oxygen and other reactants to the reaction chamber 32. Within each of the evaporation chambers, there are evaporation boats 26, 27 and 28 in the respective evaporation chambers 12, 14, and 16. While shown as three separate evaporation chambers, it is possible that the evaporation chambers may be combined in one chamber.

Generally speaking, the thermal decomposition of the respective metal organics on the substrate is accomplished in the following manner: Each different metal organic reagent is placed in the evaporation boat or reservoir. The entire assembly is flushed with an inert gas, such as nitrogen or argon. The evaporation chambers and reaction chambers are then heated to 100°-750° C. dependent on the reactants, and a flow of oxidizing gas, such as $O_2$ or tetrahydrofuran and/or a hydrolyzing gas such as methanol, ethanol, or water vapor is initiated into the reaction chamber while the chamber and substrate are maintained at that temperature. Source flows of each composition are initiated when the metal organic is sublimed or otherwise vaporized. The vapors of each metal organic are then transported to the heated substrate by natural convection or by the flow of the carrier gas. On the heated substrate, the metal organics decompose with the formation of a continuous film of metal oxide of desired composition and react with the oxidizing gas. The organo ligands remaining after deposition of the metal oxide onto the substrate may then be exhausted to a capture means as known in the art. The ligands thus captured may then be discarded or reused to form further metal organic ligands.

In the second stage of deposition, the evaporation boat temperature for each metal organic reagent is reduced to below the vaporizing or sublimation temperature of the metal organic, and the reactant gas flow is changed to pure oxygen at a flow rate of about 5-500 ml/min., and preferably 100-200 ml/min. The substrate is heated to 600-950° C. to anneal the deposited metal oxidofilm and then allowed to slowly cool in the oxygen flow for a period of 1-24 hours. The resulting superconductive film may be protected from atmospheric moisture or other contaminants by coating with a noble metal overlayer such as gold, silver, or platinum, or by treating with a silylating agent such as hexamethyldisilizane.

Representative examples for the preparation of a complex for use in the present invention are as follows:

EXAMPLE I

Synthesis of $Tl(C_5H_7O_2)Tl[tris(acetylacetonate)]$ 0.05 mol of $Tl(NO_3)_3$ is dissolved in water. $NH_4OH$ is added to the resulting solution slowly to precipitate hydroxide, and neutralize the solution. 0.15 mol (15.5 ml) of acetylacetone is added to the solution and the same is refluxed for 30 minutes. The solution is cooled, filtered, and washed with hot water to remove unreacted acetylacetone. Drying in a vacuum desiccator yields $Tl(C_5H_7O_2)_3$.

EXAMPLE II

Synthesis of $Tl(C_{11}H_{19}O_2)_3$ $(Tl(dpm)_3)$ 0.06 mol of dipivaloylmethane is dissolved in 30 ml of ethanol, and placed in a flask with a stopcock connected to an exhaust unit. 2.4 gr of NaOH is dissolved in 50 ml of 50% ethanol; the resulting solution is poured into the flask. The reaction product is continuously stirred by means of a magnetic stirrer. To this is added a solution obtained by dissolving 0.02 mol of $Tl(NO_3)_36H_2O$ in 50 ml of 50% ethanol. The flask is placed under nitrogen and the solution stirred for 2 hours. It is then distilled under reduced pressure until the solution is reduced to half of its initial volume. 350 ml of distilled water is added to separate a precipitate of $Tl(dpm)_3$, which is vacuum-filtered and dried. The crystals are re-crystallized under nitrogen from n-hexane, and vacuum-dried.

Utilizing complexes, such as those listed above, which may be prepared according to the procedures of Examples I and II, or which may be obtained from commercial sources, a high $T_c$ superconductive ceramic of the formula $[TlO_mBa_2Ca_{n-1}Cu_nO_{2n+2}; m=1,2; n=1,2,3]$ may be obtained through procedures such as those illustrated in the following Examples.

EXAMPLE III

Sufficient amounts of $Cu(dpm)_2$, $Tl(dpm)_3$, $Ca(dpm)_3$, and $Ba(fod)_3$ are each placed in an evaporation boat in an apparatus as described in connection with FIG. 1. The evaporation and reaction chambers are purged with nitrogen. Each evaporator boat is heated to the vaporizing temperature of the ligand and oxygen is introduced through the oxygen feed tube at 200 ml/min. The temperature of the reaction chamber walls are heated to and maintained at 180° C., while the deposition substrate, formed of $SiO_2$, is maintained at 300°-500° C. After 10 hours of deposition of the metal complex, the substrate is heated to about 850° C. to anneal the metal complex, and is then allowed to cool slowly while the oxygen flow is maintained. The cooled metal oxide, $TlBa_2Ca_2Cu_3O_x$ is treated with hexamethyldisilizane for protection from moisture.

EXAMPLE IV

Sufficient amounts of $Cu(hfa)_2$, $Tl(C_5H_7O_2)_3$, $Ba(fod)_3$, $Ca(dpm)_3$ are each placed on an evaporator boat in an apparatus as described in connection with FIG. 1. The evaporation and reaction chambers are purged with nitrogen. Each evaporator boat is heated to the vaporization temperature of each ligand and oxygen is introduced through the oxygen feed tube at 200 ml/min. The reaction chamber temperature containing the substrate, the substrate being formed of $SiO_2$, is maintained at 300°-500° C. After 5 hours of deposition of the oxide film, the substrate is heated to about 850° C. to anneal the metal complex, and then allowed to cool slowly. The cooled metal complex, $TlBa_2Ca_2Cu_3O_x$ is treated with hexamethyldisilizane for protection from moisture.

EXAMPLE V

Vapor deposition of Ba-Ca-Cu-O films was carried out in a horizontal, cold wall quartz reactor having individual inlet tubes for the volatile, metal organic sources $Ba(fod)_3$, $Ca(dpm)_2$, and $Cu(acac)_2$. Deposition was carried out at 5 Torr pressure with an argon carrier gas, source temperatures of 160°-210° C., and water vapor as the reactant gas. Films 5-10 μm thick were deposited on single crystal yttria-stabilized zirconia (YSZ) substrates at 600° C. and were substantially annealed for 3 hours at 800° C. in flowing oxygen saturated with water vapor. The purpose of the water vapor is to remove excess fluoride from the films.

EXAMPLE VI

Figure 3:
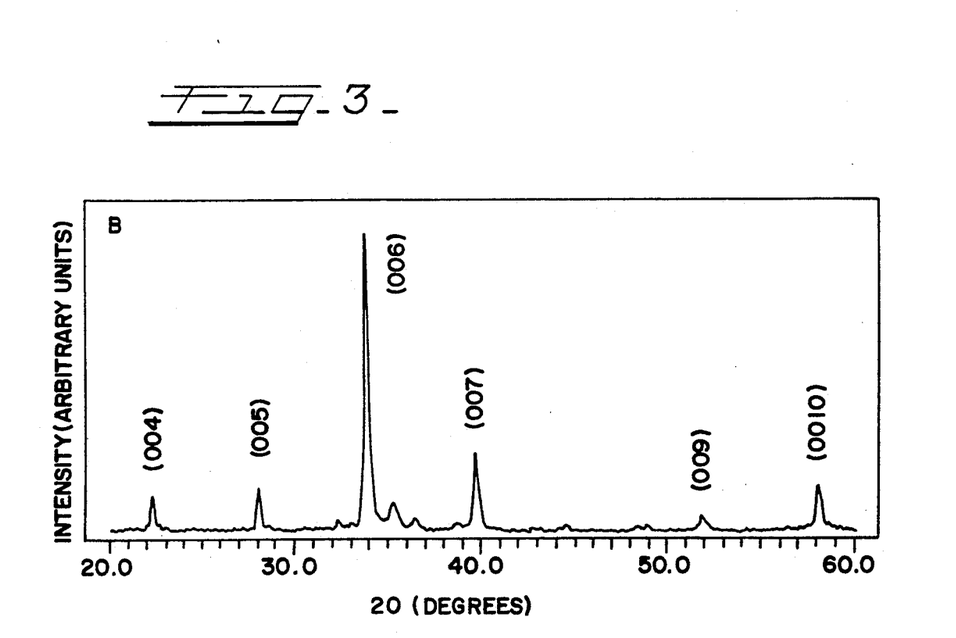
FIG. 3 shows x-ray diffraction patterns of Tl-Ba-Ca-Cu-O film on yttrium-stabilized zirconia prepared by MOCVD.
Figure 5:
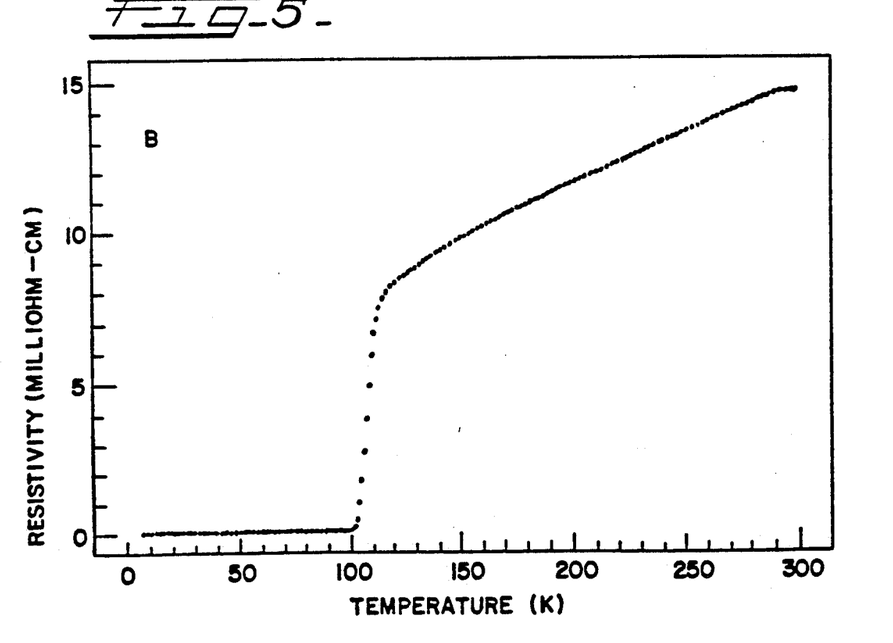
FIG. 5 is a graph of four-probe variable temperature electrical resistivity data for the film of FIG. 3.

For thallium introduction via a vapor diffusion process, the annealed Ba-Ca-Cu-O film of Example V was heated under air in a closed crucible containing a pellet of $TlBa_2Ca_2Cu_3O_x$ (a source of volatile $Tl_2O + Tl_2O_3$) for 3 min. at 880° C. and cooled slowly to room temperature. The x-ray diffraction patterns (Cu $K\alpha$) of the resulting films [FIG. 3] show them to be composed predominantly of the $TlBa_2Ca_2Cu_3O_x$ phase. The enhanced intensities of the (001) reflections indicate that the crystallite c axes are preferentially oriented perpendicular to, and the CuO planes parallel to, the substrate surface. A scanning electron micrograph of these films reveals an irregular surface with grains of $\sim 1-5$ $\mu m$ dimensions. Four-probe resistivity measurements were performed with instrumentation described previously and using 25 $\mu m$ gold wire contacts attached with gold paste. As can be seen in FIG. 5, the transition to the superconducting state in these films begin at $\sim 120K$ with $\rho = O$ at 101K. The metallic character of the transport at temperature above 120K is typical of high quality, high $T_c$ films.

EXAMPLE VII

Figure 4:
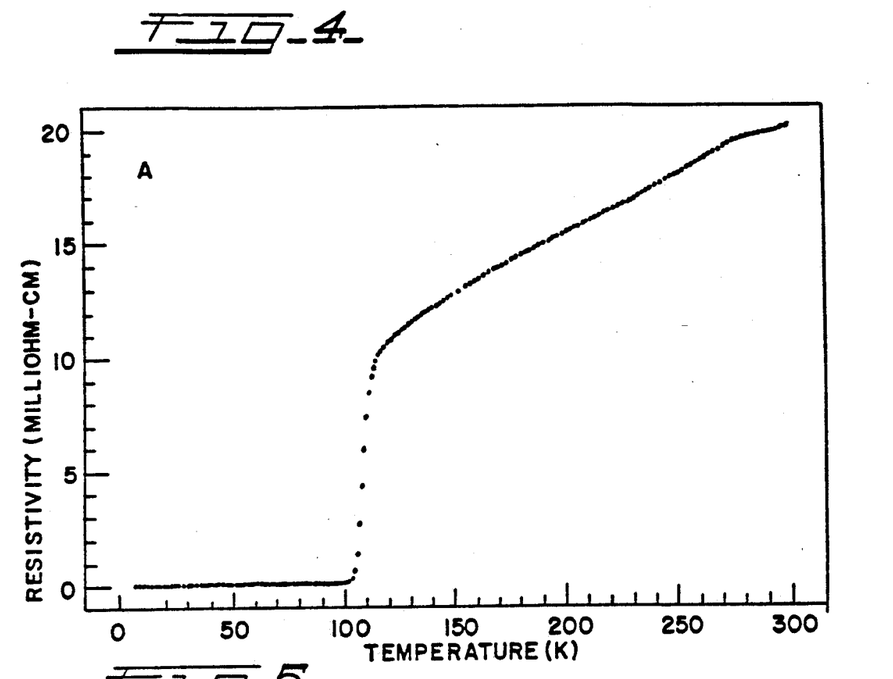
FIG. 4 is a graph of four-probe variable temperature electrical resistivity data for the film of FIG. 2.

For thallium introduction into Ba-Ca-Cu-O films by MOCVD, the volatile thallium precursor thallium cyclopentadienide $[Tl(C_5H_5)]$ was employed. Deposition was carried out at atmospheric pressure with an argon carrier gas and a water-saturated oxygen reactant gas. The source temperature was 50–80° C., and the temperature of the Ba-Ca-Cu-O substrate, 300° C. The as-deposited films are insulating and amorphous by x-ray diffraction. Annealing was carried out by rapid heating (1 min. at 800° C.) in a closed crucible or, more satisfactorily (to avoid thallium loss), in the presence of bulk $TlBa_2Ca_2Cu_3O_x$ vapor deposition, x-ray diffraction data indicate the predominance of the $TlBa_2Ca_2Cu_3O_x$ phase (with, perhaps, minor amounts of other phases) and preferential crystallite orientation. Interestingly, electron micrographs of the MOCVD-derived Tl-Ba-Ca-Cu-O films reveal smoother, less irregular surfaces. The resistivity characteristics of the MOCVD-derived films (FIG. 5) are similar to those of the MOCVD + $Tl_2O/Tl_2O_3$-derived films (FIG. 4), with a superconducting onset at $\sim 120K$ and zero resistance by 100K.

EXAMPLE VIII

Figure 6:
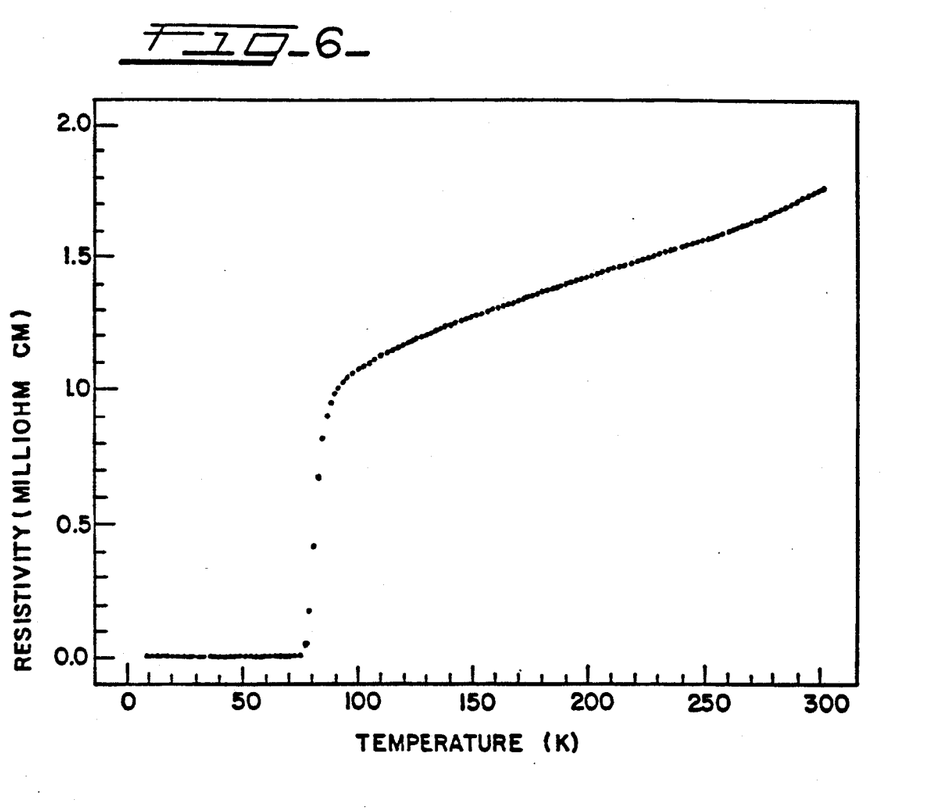
FIG. 6 is a graph of four-probe variable temperature electrical resistivity data for the film Bi$_2$(Sr,Ca)$_3$Cu$_2$O$_x$.

Deposition of Bi-Sr-Ca-Cu-O films was carried out at 2 Torr using the method of Example III (the apparatus is modified to permit four separate evaporation chambers) and the precursors $Bi(C_6H_5)_3$, $Ca(dpm)_2$, $Sr(dpm)_2$, and $Cu(acac)_2$ with source temperatures in the range 145°–230° C. and a substrate temperature of 550° C. The reactant gas was water vapor-saturated oxygen. While water vapor alone gives acceptable deposition yields of Ca, Sr, and Cu oxides, the addition of oxygen should achieve efficient, simultaneous deposition of Bi. Presumably the hydrolytic stability of the Bi-phenyl bond is too great to allow efficient protonolytic cleavage. Annealing of the films in flowing oxygen for 0.5 hours at 600° C. and 0.5 hours at 865° C. yields 3–6 $\mu m$ thick films which, as shown, x-ray diffraction consists largely of the $T_c = 85K$ $Bi_2(Sr,Ca)_3Cu_2O_x$ phase. Variable-temperature four-probe resistivity measurements were performed on the annealed films using 25 $\mu m$ gold wire contacts held in place with gold paste. Data for a typical MOCVD-derived film are shown in FIG. 6. As is characteristic of relatively high quality high $T_c$ films, charge transport at temperatures above $\sim 110K$ is metallic, i.e., $dp/dT > 0$. FIG. 6 demonstrates that the onset of the superconducting state begins at $\sim 110K$ with attainment of zero resistance at 75K.

These results show that high $T_c$ superconducting Tl-Ba-Ca-Cu-O films with good electrical properties can be synthesized either by a purely MOCVD approach using volatile Tl,Ba,Ca, and Cu molecular precursors or by an MOCVD approach in which Tl may be introduced by vapor diffusion.

Further, high $T_c$ superconducting Bi-Sr-Ca-Cu-O films with $T_c$ values in the region of 80° K. to 110° K. with good electrical properties can be prepared in an efficient MOCVD process using appropriately design metal organic precursors and reaction conditions.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments and equivalents falling within the scope of the appended claims.

Various features of the invention are set forth in the following claims.

What is claimed:

1. A method for the preparation of a superconducting ceramic film by chemical vapor deposition comprising the steps of:

(a) flushing at least one vaporization chamber with an inert gas;

(b) placing at least three metal organic compounds of the formula in said chamber, where R and R' are selected from the group consisting of alkyls, alkoxides, and fluorinated alkyls, the first metal organic compound having M = Ba, the second metal organic compound having M = Cu, and the third metal organic compound having M = Ca;

(c) heating each metal organic compound to its vaporizing temperature to cause a source flow comprising vapors of each metal organic compound in said chamber;

(e) heat a substrate to a temperature of 400°–800° C;

(d) transporting said vapors into a deposition chamber;

(f) initiating a flow of oxygen into said deposition chamber;

(g) depositing a film from said vapors onto said substrate in said deposition chamber;

(h) terminating said source flow;

(i) adjusting the temperature of said substrate to the range of 600°-950° C. to thereby anneal said film; and (j) heat said annealed film in the range of 600°-950° C. under air in a closed circular vessel with TlBa$_2$Ca$_2$Cu$_3$O$_x$ and cool to form said superconducting ceramic film of TlO$_m$Bs$_2$Ca$_{n-1}$Cu$_n$O$_{2n+2}$; wherein m=1,2; n=1,2,3.

2. The method of claim 1 further including the steps of flushing three separate vaporization chambers and placing each of said three metal organic compounds in a different one of said separate vaporization chambers.

3. The method of claim 1 further including the step of adding water vapor to the deposition chamber with said flow of oxygen.

4. The method of claim 1 wherein the first metal organic compound is selected from the group consisting of:

Ba(fod)$_3$, Ba(dfh)$_3$, and Ba(dpm)$_2$;

the second metal organic compound is selected from the group consisting of Cu(dpm)$_2$ and Cu(hfa)$_2$; and the third metal organic compound is selected from the group consisting of Ca(dpm)$_3$, Ca(fod)$_3$, and Ca(C$_5$H$_7$O$_2$)$_3$.

5. The method of claim 1 wherein R and R' are selected from the group consisting of —CH$_3$, —C(CH$_3$)$_3$, —CF$_3$, —CF$_2$CF$_2$, —C$_5$H$_7$O$_2$, and CF$_2$CF$_3$.

6. A method for the preparation of a superconducting ceramic film by chemical vapor deposition comprising the steps of:

(a) flushing at least three separated vaporization chambers with an inert gas;

(b) placing at least three metal organic compounds of the formula one in each of said chambers, where R and R' are selected from the group consisting of alkyls, alkoxides, and fluorinated alkyls, the first metal organic compound having M=Ba and being placed in a first flushed vaporization chamber, the second metal organic compound having M=Cu and being placed in a second flushed vaporization chamber, the third metal organic compound having M=Ca and being placed in a third flushed vaporization chamber;

(c) heating each metal organic compound to its vaporization temperature to cause a source flow comprising a vapor of each metal organic compound in each respective chamber;

(d) transporting said vapors into a heated deposition chamber;

(e) initiating a flow of oxygen of about 180-200 liters/hr. into said deposition chamber;

(f) depositing a film from said vapors onto a substrate in said deposition chamber;

(g) terminating said source flow;

(h) maintaining said oxygen flow; and (i) increasing the temperature of said substrate to the range of 600°-950° C. to thereby anneal said film maintaining the temperature of the annealed film at in the range of 200°-400° C., contacting said annealed film with gaseous Tl R" where R" is selected from the group consisting of alkyl, aryl, alkoxide, and halide and annealing in the presence of TlBa$_2$Ca$_2$Cu$_3$O$_x$ to result in said superconducting ceramic film of TlO$_m$Ba$_2$Ca$_{n-1}$Cu$_n$O$_{2n+2}$; wherein m=1,2; n=1,2,3.

7. The method of claim 6 further including the step of adding water vapor to the deposition chamber with said flow of oxygen.

8. The method of claim 6 wherein Tl R" is Tl(C$_5$H$_5$).

9. The method of claim 6 wherein the first metal organic compound is selected from the group consisting of:

Ba(fod)$_3$, Ba(dfh)$_3$, and Ba(dpm)$_2$ the second metal organic compound is selected from the group consisting of Cu(dpm)$_2$ and Cu(hfa)$_2$; and the third metal organic compound is selected from the group consisting of Ca(dpm)$_3$, Ca(fod)$_3$, and Ca(C$_5$H$_7$O$_2$)$_3$.

10. The method of claim 6 wherein R and R' are selected from the group consisting of —CH$_3$, —C(CH$_3$)$_3$, —CF$_3$, —CF$_2$CF$_2$CR$_3$, —C$_5$H$_7$O$_2$, and CF$_2$CF$_3$.

* * * * *

UNITED STATES PATENT AND TRADEMARK OFFICE
CERTIFICATE OF CORRECTION

PATENT NO. : 5,185,317
DATED : February 9, 1993
INVENTOR(S) : Wessels, et al.

It is certified that error appears in the above-identified patent and that said Letters Patent is hereby corrected as shown below:

Column 2, Line 21, "n32 1,2,3" should be --n = 1,2,3--.

Column 2, Line 46, "n-1,2,3" should be --n = 1,2,3--.

Column 2, Line 52, "n32, 1,2,3" should be --n = 1,2,3--.

Column 3, Line 67, "31" should be -- - --.

Column 5, Line 22, "100°" should be --100°C--.

Column 5, Line 47, "600" should be --600°C--.

Column 6, Line 38, "300°" should be --300°C--.

Column 6, Line 55, "300°" should be --300°C--.

Column 9, Line 11, "600°C" should be --600°C--.

Column 9, Line 50, "-CF$_2$CF$_2$," should be --CF$_2$CF$_2$CF$_3$,--.

Signed and Sealed this

First Day of March, 1994

Attest:

BRUCE LEHMAN

*Attesting Officer*       *Commissioner of Patents and Trademarks*